United States Patent
Hida et al.

(10) Patent No.: US 10,505,185 B2
(45) Date of Patent: Dec. 10, 2019

(54) SOLID ELECTROLYTE AND ALL-SOLID-STATE BATTERY

(71) Applicant: FUJITSU LIMITED, Kawasaki-shi, Kanagawa (JP)

(72) Inventors: Masaharu Hida, Atsugi (JP); Satoru Watanabe, Atsugi (JP); Tamotsu Yamamoto, Tachikawa (JP)

(73) Assignee: FUJITSU LIMITED, Kawasaki (JP)

( * ) Notice: Subject to any disclaimer, the term of this patent is extended or adjusted under 35 U.S.C. 154(b) by 189 days.

(21) Appl. No.: 15/657,437

(22) Filed: Jul. 24, 2017

(65) Prior Publication Data

US 2017/0324087 A1    Nov. 9, 2017

Related U.S. Application Data

(63) Continuation of application No. PCT/JP2015/052829, filed on Feb. 2, 2015.

(51) Int. Cl.

| | |
|---|---|
| *H01M 4/46* | (2006.01) |
| *H01M 4/58* | (2010.01) |
| *H01M 10/0525* | (2010.01) |
| *G01N 21/35* | (2014.01) |
| *C01F 7/00* | (2006.01) |
| *H01M 10/0562* | (2010.01) |
| *H01M 10/052* | (2010.01) |
| *C01B 25/41* | (2006.01) |
| *H01B 1/08* | (2006.01) |
| *G01N 21/3563* | (2014.01) |

(52) U.S. Cl.
CPC .......... *H01M 4/463* (2013.01); *C01B 25/41* (2013.01); *H01M 4/5825* (2013.01); *H01M 10/052* (2013.01); *H01M 10/0562* (2013.01); *C01F 7/002* (2013.01); *G01N 21/3563* (2013.01); *G01N 2021/3595* (2013.01); *H01B 1/08* (2013.01); *H01M 10/0525* (2013.01); *H01M 2300/0068* (2013.01); *Y02T 10/7011* (2013.01)

(58) Field of Classification Search
None
See application file for complete search history.

(56) References Cited

U.S. PATENT DOCUMENTS

| | | |
|---|---|---|
| 2006/0210882 A1 | 9/2006 | Ugaji |
| 2009/0162755 A1 | 6/2009 | Neudecker |
| 2012/0214064 A1 | 8/2012 | Sabi |
| 2014/0072727 A1* | 3/2014 | Hayden ............... C23C 14/24 427/570 |

(Continued)

FOREIGN PATENT DOCUMENTS

| | | |
|---|---|---|
| JP | 2005-038843 A1 | 2/2005 |
| JP | 2011-511399 A1 | 4/2011 |

(Continued)

OTHER PUBLICATIONS

Kurita et al. "Stable Interfaces of Solid Electrolytes with LiFePO4 Cathode During Charge and Discharge Operations". Abstract #438, 224th ECS Meeting, The Electrochemical Society 2013 (Year: 2013).*

(Continued)

*Primary Examiner* — Christopher P Domone
(74) *Attorney, Agent, or Firm* — Kratz, Quintos & Hanson, LLP

(57) ABSTRACT

A solid electrolyte including Li, Al, P, O, and N, wherein the solid electrolyte has a $P_2O_7$ structure.

4 Claims, 6 Drawing Sheets

(56) References Cited

U.S. PATENT DOCUMENTS

| | | |
|---|---|---|
| 2014/0287160 A1 | 9/2014 | Hayden |
| 2015/0180085 A1 | 6/2015 | Homma |
| 2016/0172704 A1 | 6/2016 | Watanabe |

FOREIGN PATENT DOCUMENTS

| | | |
|---|---|---|
| JP | 2011-108533 A1 | 6/2011 |
| JP | 2014-525989 A1 | 10/2014 |
| WO | 2013/011327 A2 | 1/2013 |
| WO | 2014041669 A1 | 3/2014 |
| WO | 2015029103 A1 | 3/2015 |

OTHER PUBLICATIONS

Poisson et al. Crystal Structure and Cation Transport Properties of the Layered Monodiphosphates Li9M3(P2O7)3(PO4)2 (M=Al, Ga, Cr, Fe). p. 1-10. 1998. (Year: 1998).*

X. Yu, et al.; "A Stable Thin-Film Lithium Electrolyte: Lithium Phosphorus Oxynitride;" J. Electrochem. Soc.; vol. 144; No. 2; Feb. 1997; pp. 524-532 (9 Sheets)/Cited in International Search Report/ p. 2 of specification.

Q. Kuang, et al.; Synthesis and electrochemical properties of layered lithium monodiphosphate Li9V3—xAlx(P2O7)3 (PO4)2 solid solutions; Electrochimica Acta; vol. 58; 2011; pp. 296-302 (7 Sheets)/Cited in International Search Report.

S. Poisson, et al.; Crystal Structure and Cation Transport Properties of the Layered Monodiphosphates: Li9M3 (P2O7)3(PO4)2(M=Al, Ga, Cr, Fe); Journal of Solid State Chemistry; vol. 138; 1998; pp. 32-40 (9 Sheets)/Cited in International Search Report.

International Search Report for International Application No. PCT/JP2015/052829 dated Apr. 21, 2015.

Office Action of Japanese Patent Application No. 2016-572960: Notification of Reasons for Refusal dated Aug. 28, 2018 (5 pages, 4 pages translation, 9 pages total).

* cited by examiner

SOLID ELECTROLYTE AND ALL-SOLID-STATE BATTERY

CROSS-REFERENCE TO RELATED APPLICATION

This application is a continuation application of International Application PCT/JP2015/052829 filed on Feb. 2, 2015 and designated the U.S., the entire contents of which are incorporated herein by reference.

FIELD

The embodiments discussed herein relate to a solid electrolyte and an all-solid-state battery.

BACKGROUND

Recently, secondary batteries configured to store electric energy have been attracted attentions for application to hybrid cars, or electric cards. As an energy saving technology, moreover, there are interests in the energy harvesting technology that generates electricity from small environmental energy. The secondary batteries capable of storing and supplying generated electric energy have been attracted attentions because there is a limitless possibility for various applications of the secondary batteries.

Attentions have been drawn to particularly all-solid-state batteries, which are secondary batteries and do not use a liquid for an electrolyte, in view of safety. All-solid-state batteries currently available on the market have a structure where $LiCoO_2$ is used for a cathode, LiPON (lithium phosphorus oxynitride) is used for an electrolyte, and Li is used for an anode. LiPON is a solid electrolyte having a high lithium ion conductivity.

In order to widen applicable fields, such batteries are always desired to increase an energy density. In order to improve an energy density of a battery, there are two ways, an increase in a capacity density and an increase in operating voltage.

When an increase in operating voltage is performed, there is a report that LiPON that is an electrolyte of an all-solid-state battery currently commercially available is decomposed with voltage of 5.6 V or higher (see, for example, Xiaohua Yu, J. B. Bates, G. E. Jellison, Jr. and F. X. Hart, J. Electrochem. Soc., Vol. 144, 524 (1997)). Considering safety, therefore, used voltage of an all-solid-state battery using LiPON as a solid electrolyte is preferably kept about 5.0 V.

Moreover, proposed as a solid electrolyte used for an all-solid-state battery is a solid electrolyte which uses LiPON as a base and is modified by adding various elements (see, for example, Japanese Patent Application Laid-Open (JP-A) Nos. 2005-38843 and 2011-511399).

SUMMARY

The disclosed solid electrolyte includes Li, Al, P, O, and N, where the solid electrolyte has a $P_2O_7$ structure.

The disclosed all-solid-state battery includes a cathode active material layer, an anode active material layer, and a solid electrolyte layer disposed between the cathode active material layer and the anode active material layer, wherein the solid electrolyte layer is a layer formed of the disclosed solid electrolyte.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

A solid electrolyte which uses LiPON as a base and is modified by adding various elements uses lithium phosphate as a target material, similarly to LiPON. Therefore, it is assumed that such a solid electrolyte is also difficult to correspond to an increase in voltage for use.

The disclosed embodiments aim to solve the above-described various problems existing in the art, and to achieve the following object. Specifically, the present disclosure has an object to provide a solid electrolyte that has a high lithium conductivity and can be used with high voltage, and an all-solid-state battery using the solid electrolyte.

The disclosed solid electrolyte can solve the above-described various problems existing in the art, can achieve the above-described object, and can provide a solid electrolyte that has a high lithium ion conductivity and can be used with high voltage.

The disclosed all-solid-state battery can solve the above-described various problems existing in the art, can achieve the above-described object, and can provide an all-solid-state battery that has a high lithium ion conductivity and can be used with high voltage.

(Solid Electrolyte)

The disclosed solid electrolyte includes lithium (Li), aluminium (Al), phosphorus (P), oxygen (O), and nitrogen (N), and has a $P_2O_7$ structure.

Figure 1:
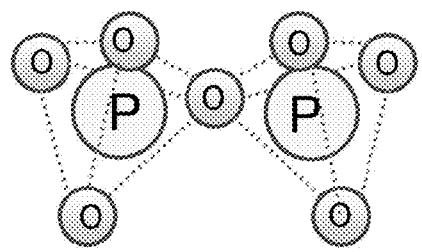
FIG. 1 is a schematic view illustrating a $P_2O_7$ structure.

The $P_2O_7$ structure has a structure as illustrated in FIG. 1. Specifically, the $P_2O_7$ structure is a structure where two regular tetrahedrons each having phosphorus (P) as a center and four oxygens (O) as apexes are connected with shearing one oxygen (O).

The solid electrolyte is preferably represented by Compositional Formula (1) below because a stable solid electrolyte can be obtained.

$$Li_{9+a}Al_{3+b}P_{8-c}O_{29-d}N_e \quad \text{Compositional Formula (1)}$$

Compositional Formula (1) satisfies $0 \leq a \leq 5$, $-1 \leq b \leq 1$, $0 \leq c \leq 2$, $0 \leq d \leq 5$, and $0 < e \leq 5$.

In infrared spectroscopy of the solid electrolyte, a vibration spectrum originated from the $P_2O_7$ structure is preferably observed at 720 cm$^{-1}$ to 790 cm$^{-1}$. The observation of the vibration spectrum confirms that the solid electrolyte has the $P_2O_7$ structure.

Figure 2A:
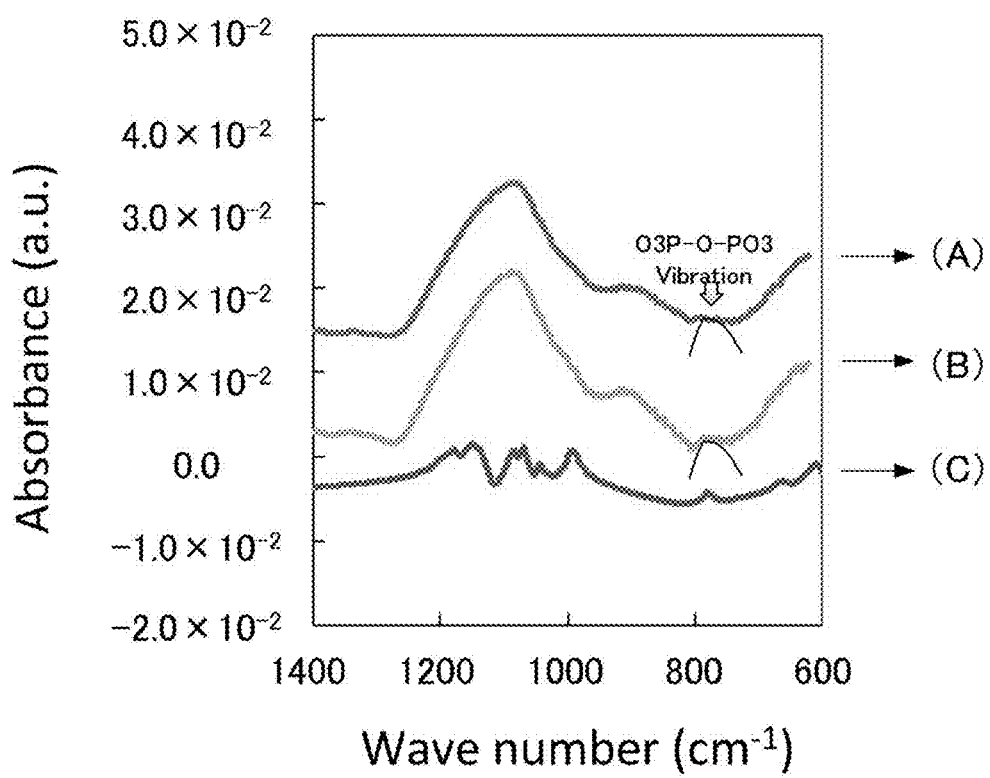
FIG. 2A is a graph depicting an infrared spectrum.
Figure 2B:
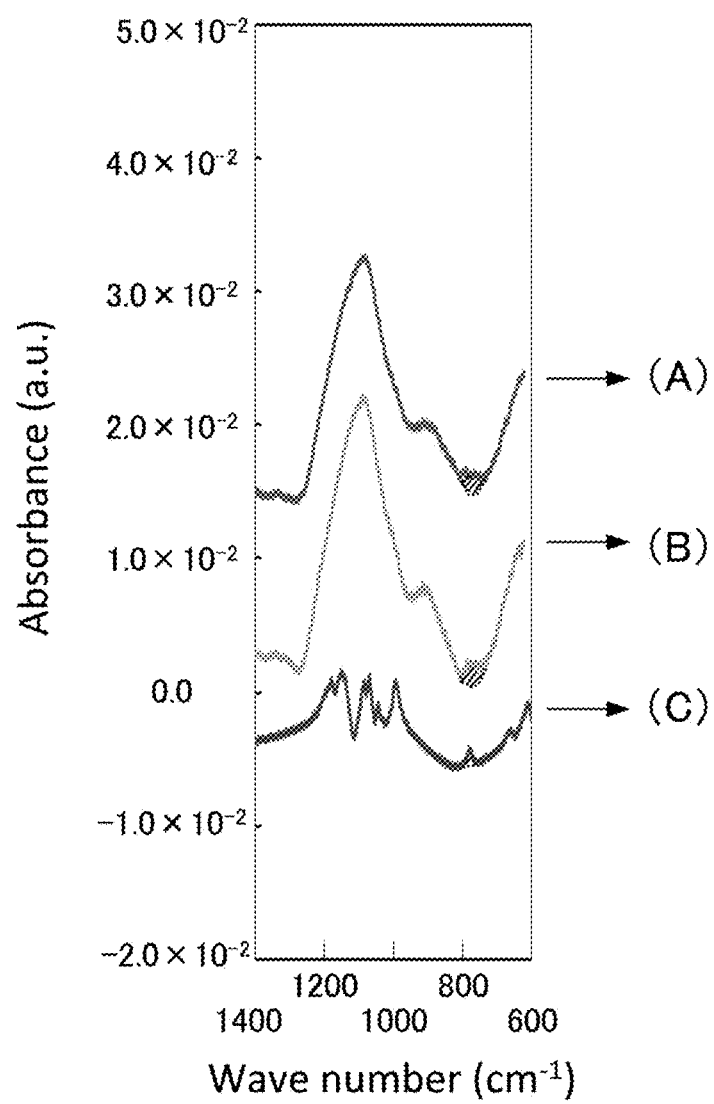
FIG. 2B is a graph where the graph of FIG. 2A is elongated in a vertical direction.

As depicted in FIG. 2A, for example, a vibration spectrum of a $P_2O_7$ structure is observed at 720 cm$^{-1}$ to 790 cm$^{-1}$ in infrared spectroscopy. FIG. 2B is a graph where FIG. 2A is elongated in the vertical direction, and depicts an absorption by the vibration spectrum of the $P_2O_7$ structure with a diagonal line.

In FIGS. 2A and 2B, (A), (B), and (C) are as follows.

(A) is an infrared spectrum of a thin film of the solid electrolyte produced by sputtering. The thin film of the solid electrolyte is produced by sputtering using $Li_9Al_3(P_2O_7)_3(PO_4)_2$ as a target material in a plasma atmosphere including $N_2$.

(B) is an infrared spectrum of a thin film of $Li_9Al_3(P_2O_7)_3(PO_4)_2$ produced by sputtering.

(C) is an infrared spectrum of a powder of $Li_9Al_3(P_2O_7)_3(PO_4)_2$ that is the target material used in the production of the samples of (A) and (B) above.

An amount of nitrogen (N) in the solid electrolyte is preferably 8 atm % or less because a solid electrolyte having stable performance can be obtained. The amount of nitrogen in the solid electrolyte can be measured by XPS analysis. The measurement can be performed by means of Quantera SXM available from ULVAC-PHI, Inc.

A production method of the solid electrolyte is not particularly limited and may be appropriately selected depending on the intended purpose, but the production method is preferably sputtering.

Examples of a method for producing the solid electrolyte through the sputtering include a method where $Li_9Al_3(P_2O_7)_3(PO_4)_2$ is used as a target material and a thin film of the solid electrolyte is formed in a plasma atmosphere including $N_2$. In this method, part of O atoms of $Li_9Al_3(P_2O_7)_3(PO_4)_2$ are substituted with N atoms in the process of film formation.

(All-Solid-State Battery)

The disclosed all-solid-state battery includes a cathode active material layer, an anode active material layer, and a solid electrolyte layer disposed between the cathode active material layer and the anode active material layer, and may further include other members according to the necessity.

<Cathode Active Material Layer>

The cathode active material layer is not particularly limited and may be appropriately selected depending on the intended purpose, except that the cathode active material layer is, for example, a layer including a cathode active material.

The cathode active material layer may be the cathode active material itself.

The cathode active material is not particularly limited and may be appropriately selected depending on the intended purpose. Examples of the cathode active material include lithium-containing composite oxides. The lithium-containing composite oxides are not particularly limited and may be appropriately selected depending on the intended purpose, as long as the lithium-containing composite oxides are composite oxides each including lithium and another metal. Examples of the lithium-containing composite oxides include $LiCoO_2$, $LiNiO_2$, $LiCrO_2$, $LiVO_2$, $LiM_xMn_{2-x}O_4$ (M is at least one of Co, Ni, Fe, Cr, and Cu, and $0 \leq x < 2$), $LiFePO_4$, $LiCoPO_4$, and $LiNiPO_4$.

The average thickness of the cathode active material layer is not particularly limited, but may be appropriately selected, for example, within a range of about 0.01 μm to about 10 μm depending on the intended capacity or shape of the battery.

A formation method of the cathode active material layer is not particularly limited and may be appropriately selected depending on the intended purpose. Examples of the formation method include sputtering using a target material of the cathode active material.

<Solid Electrolyte Layer>

The solid electrolyte is formed of the disclosed solid electrolyte.

The average thickness of the solid electrolyte layer is not particularly limited and may be appropriately selected depending on the intended purpose. The average thickness of the solid electrolyte layer is preferably from 0.05 μm to 3.0 μm, more preferably from 0.1 μm to 2.0 μm, and particularly preferably from 0.5 μm to 1.5 μm.

A formation method of the solid electrolyte layer is not particularly limited and may be appropriately selected depending on the intended purpose, but the formation method is preferably sputtering.

Examples of a method for forming the solid electrolyte layer through the sputtering include a method where a fin film of the solid electrolyte is formed using $Li_9Al_3(P_2O_7)_3(PO_4)_2$ as a target material in a plasma atmosphere including $N_2$. In this method, part of O atoms of $Li_9Al_3(P_2O_7)_3(PO_4)_2$ are replaced with N atoms in the process of film formation.

<Anode Active Material Layer>

The anode active material layer is not particularly limited and may be appropriately selected depending on the intended purpose, as long as the anode active material layer is, for example, a layer including an anode active material.

The anode active material layer may be the anode active material itself.

The anode active material is not particularly limited and may be appropriately selected depending on the intended purpose. Examples of the anode active material include lithium, lithium alloys, $Li_4Ti_5O_{12}$, amorphous carbon, natural graphite, and artificial graphite.

The average thickness of the anode active material layer is not particularly limited and may be appropriately selected depending on the intended purpose. The average thickness of the anode active material is preferably from 0.05 μm to 3.0 μm, more preferably from 0.1 μm to 2.0 μm, and particularly preferably from 0.5 μm to 1.5 μm.

A formation method of the anode active material layer is not particularly limited and may be appropriately selected depending on the intended purpose. Examples of the formation method include sputtering using a target material of the anode active material, and a method where the anode active material is subjected to compression molding.

<Other Members>

The above-mentioned other members are not particularly limited and may be appropriately selected depending on the intended purpose. Examples of the above-mentioned other members include a cathode current collector, an anode current collector, and a battery case.

<<Cathode Current Collector>>

A size and structure of the cathode current collector are not particularly limited and may be appropriately selected depending on the intended purpose.

Examples of a material of the cathode current collector include die steel, stainless steel, aluminium, aluminium alloys, titanium alloys, copper, and nickel.

Examples of a shape of the cathode current collector include foils, plates, and meshes.

<<Anode Current Collector>>

A size and structure of the anode current collector are not particularly limited and may be appropriately selected depending on the intended purpose.

Examples of a material of the anode current collector include die steel, gold, indium, nickel, copper, and stainless steel.

Examples of a shape of the anode current collector include foils, plates, and meshes.

<<Battery Case>>

The battery case is not particularly limited and may be appropriately selected depending on the intended purpose. Examples of the battery case include known laminate films usable for conventional all-solid-state batteries. Examples of the laminate films include laminate films formed of a resin, and films each prepared by depositing metal on a laminate film formed of a resin through vapor deposition.

A shape of the all-solid-state battery is not particularly limited and may be appropriately selected depending on the intended purpose. Examples of the shape include cylinder shapes, square shapes, button shapes, coin shapes, and flat shapes.

The all-solid-state battery is preferably a so-called thin-film all-solid-state battery, in which the cathode active material layer, the solid electrolyte layer, and the anode active material layer are laminated by a vapor phase method, because such an all-solid-state battery excels in a cycle service life.

The all-solid-state battery has a high lithium ion conductivity and can be used with high voltage. Therefore, the all-solid-state battery can be suitably used as a secondary battery.

Figure 3:
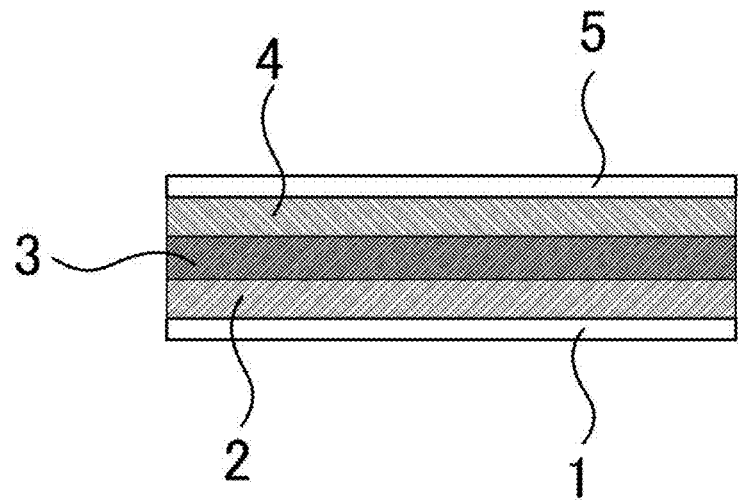
FIG. 3 is a schematic cross-sectional view illustrating one example of the disclosed all-solid-state battery.

FIG. 3 is a schematic cross-sectional view of one example of the disclosed all-solid-state battery. In the all-solid-state battery of FIG. 3, a cathode active material layer 2, a solid electrolyte layer 3, an anode active material layer 4, and an anode current collector 5 are laminated in this order on a cathode current collector 1.

EXAMPLES

Examples of the disclosed technology will be described hereinafter, but the disclosed technology shall not be limited to Examples below in any way.

For production of each layer, E-400 available from CANON ANELVA CORPORATION was used.

For a measurement of a lithium ion conductivity, PGSTAT30 available from AUTOLAB was used.

For a measurement of an amount of a nitrogen of a solid electrolyte, Quantera SXM available from ULVAC-PHI, Inc. was used.

For a measurement of a spectrum of XPS, Quantera SXM available from ULVAC-PHI, Inc. was used.

For a measurement of infrared spectroscopy, Nicolet8700 available from Thermo Fisher Scientific K.K. was used.

For a measurement of cyclic voltammetry (CV), PGSTAT30 available from AUTOLAB was used.

For a measurement of charge-discharge properties, TOSCAT-3100U available from TOYO SYSTEM CO., LTD. was used.

Example 1

A bottom electrode (average thickness: 200 nm, Pt/Ti) was formed by sputtering on a Si wafer with an oxide film. Subsequently, a solid electrolyte layer (average thickness: 1.2 μm) was formed by sputtering on the bottom electrode. Subsequently, an upper electrode (average thickness: 2.0 μm, Li, size: 5 mm×5 mm) was formed by vapor deposition on the solid electrolyte layer.

For the formation of the solid electrolyte layer by sputtering, 3 samples were produced by using $Li_9Al_3(P_2O_7)_3(PO_4)_2$ as a target material, and using 3 kinds of gas which had ratios (volume ratios) between argon gas and nitrogen gas being 100:0, 50:50, and 0:100.

Figure 4:
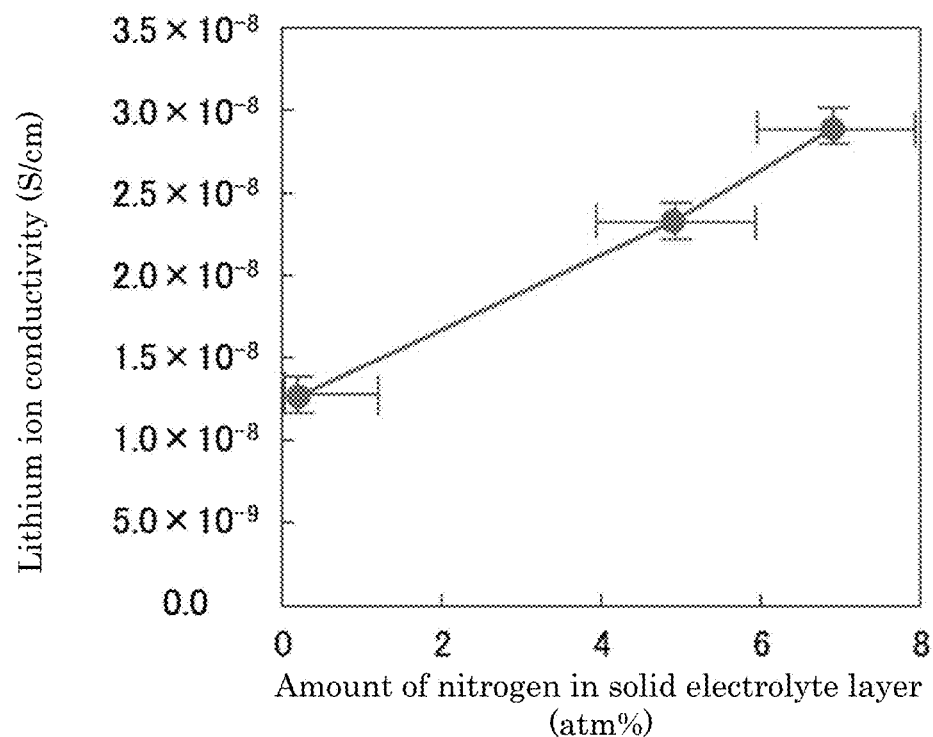
FIG. 4 is a graph depicting a relationship between an amount of nitrogen and a lithium ion conductivity.

The lithium ion conductivity of the produced samples is presented in FIG. 4. It can be found that the lithium ion conductivity is improved as an amount of nitrogen in the solid electrolyte layer increases. However, the amount of nitrogen in the solid electrolyte reaches its limit at about 8 atm % because of the solid solubility limit.

Figure 5:
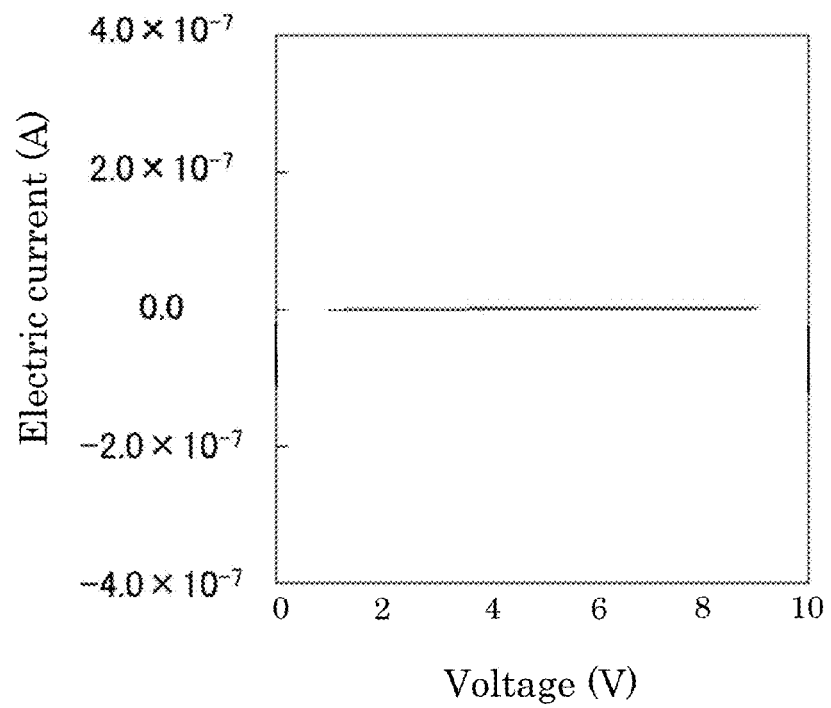
FIG. 5 is a graph depicting the cyclic voltammetric measurement result t.

The cyclic voltammetric (CV) measurement result of the sample having the solid electrolyte layer in which an amount of nitrogen is 7 atm % is presented in FIG. 5. No peak due to oxidization and reduction was observed in the range of 1 V to 9 V, it was understood that the solid electrolyte layer was a stable solid electrolyte layer.

Figure 6:
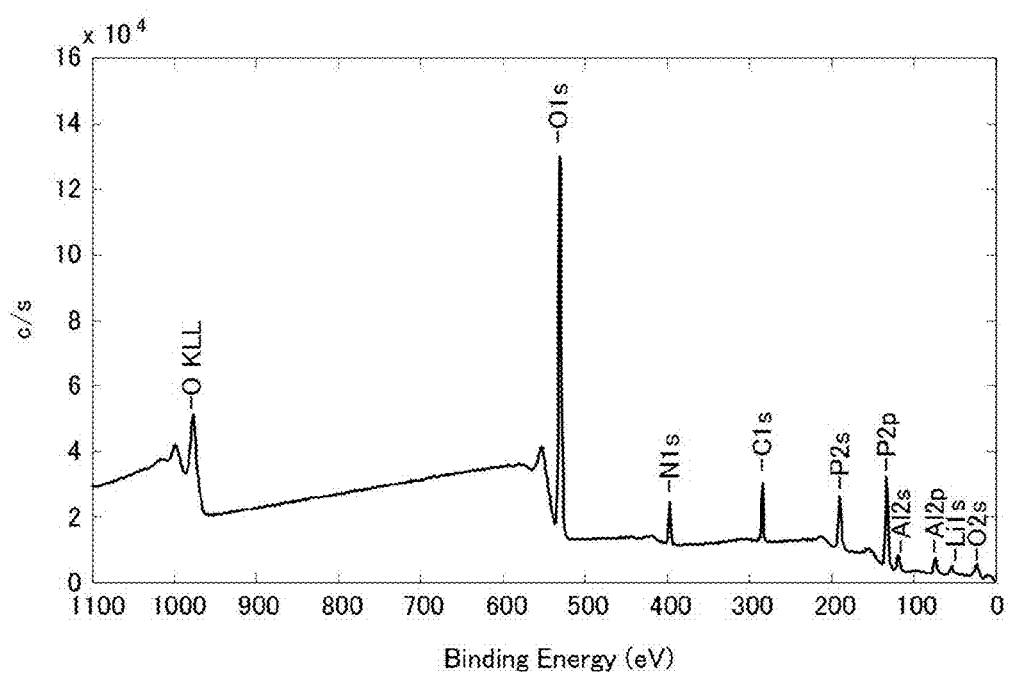
FIG. 6 is a graph depicting an XPS spectrum.

Moreover, an XPS spectrum of the solid electrolyte layer in which an amount of nitrogen is 7 atm % is presented in FIG. 6.

In infrared spectroscopy of the obtained solid electrolyte layer, a vibration spectrum derived from the $P_2O_7$ structure was observed at 720 cm$^{-1}$ to 790 cm$^{-1}$.

As described above, it was able to confirm that the solid electrolyte layers produced at the argon gas:nitrogen gas ratios (volume ratios) of 50:50 and 0:100 included Li, Al, P, and O derived from $Li_9Al_3(P_2O_7)_3(PO_4)_2$ that was the target material, included N derived from nitrogen gas, and were solid electrolyte having a $P_2O_7$ structure.

Example 2

A cathode current collector (average thickness: 200 nm, Pt/Ti) was formed by sputtering on a Si wafer with an oxide film. Subsequently, a cathode active material layer (average thickness: 100 nm, LiFePO$_4$) was formed by sputtering. Subsequently, a solid electrolyte layer (average thickness: 1.2 μm) was formed by sputtering on the cathode active material layer. Subsequently, an anode active material layer (average thickness: 2.0 μm, Li, size: 5 mm×5 mm) was formed by vapor deposition on the solid electrolyte layer. As described above, an all-solid-state secondary battery was obtained.

The formation of the solid electrolyte layer by sputtering was performed by using $Li_9Al_3(P_2O_7)_3(PO_4)_2$ as a target material at a argon gas:nitrogen gas ratio (volume ratio) of 0:100. An amount of nitrogen in the obtained solid electrolyte layer was 7 atm %.

Charge-discharge properties of the obtained all-solid-state secondary battery were measured. The results are presented in FIG. 7.

Comparative Example 1

An all-solid-state secondary battery was obtained in the same manner as in Example 2, except that the gas ratio at the time of the formation of the solid electrolyte layer by sputtering was changed to argon gas:nitrogen gas=100:0 (volume ratio). The obtained solid electrolyte layer was so-called LAPP to which the composition of the target material was reflected.

Charge-discharge properties of the obtained all-solid-state secondary battery were measured. The results are presented in FIG. 8.

Figure 7:
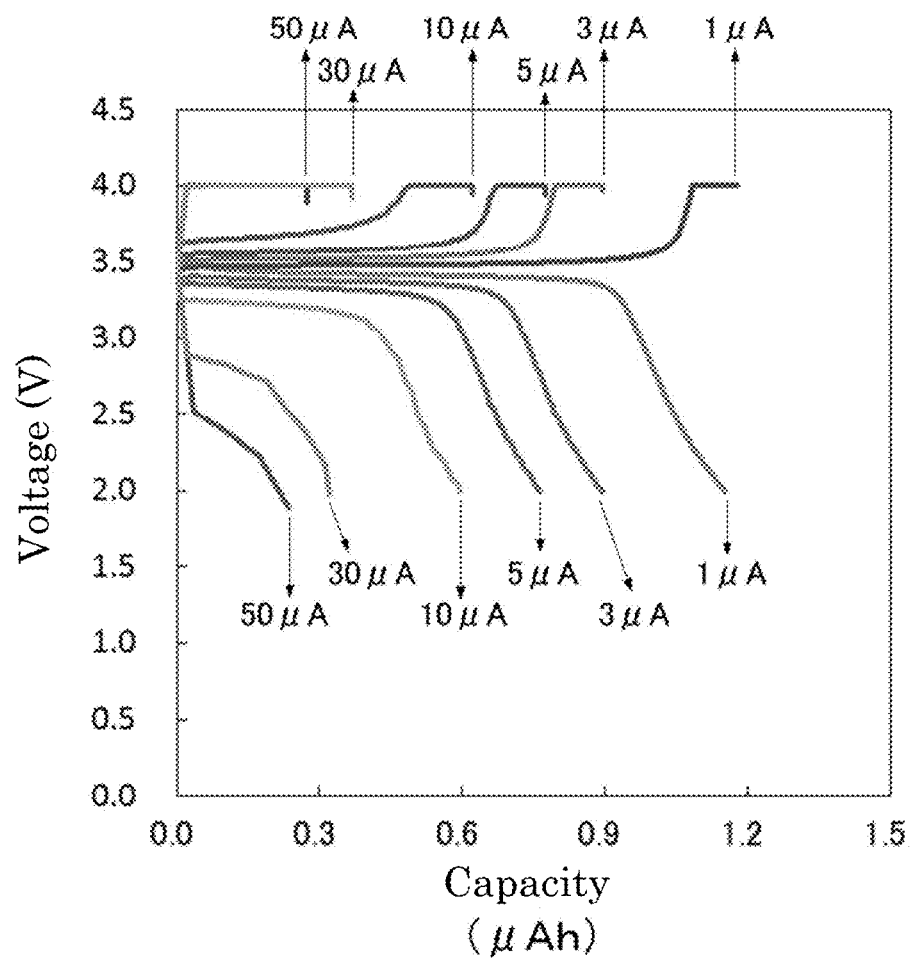
FIG. 7 is a graph depicting the measurement result of charge-discharge properties of the all-solid-state secondary battery of Example 2.
Figure 8:
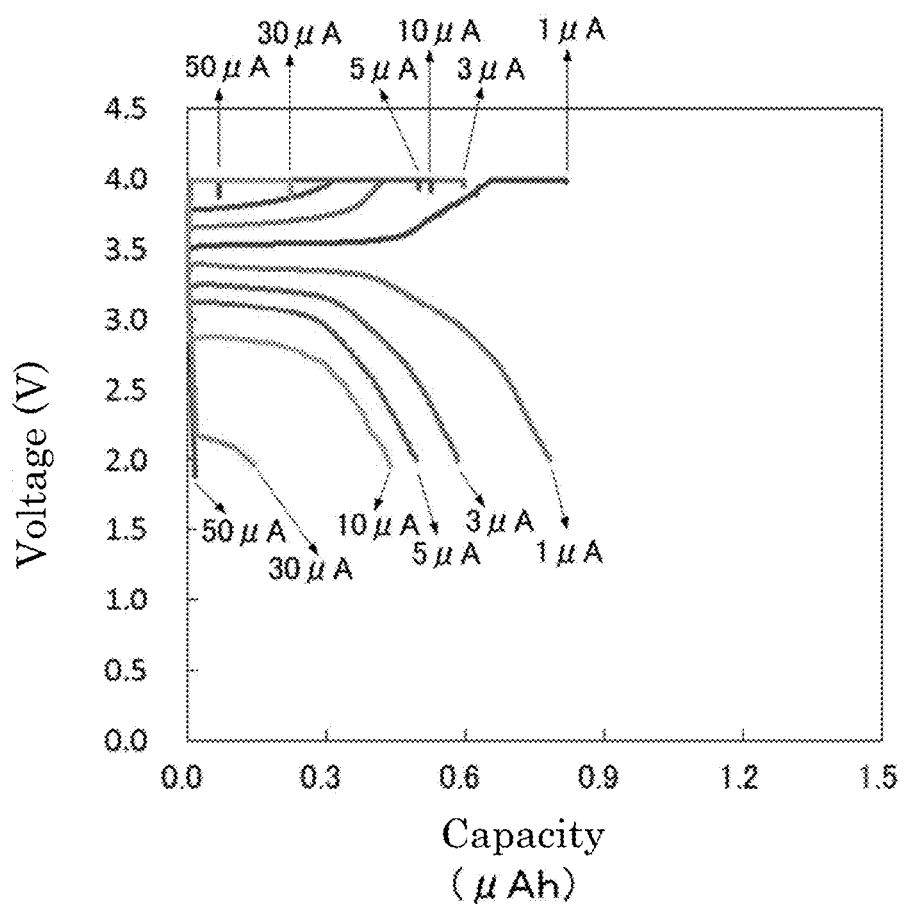
FIG. 8 is a graph depicting the measurement result of charge-discharge properties of the all-solid-state secondary battery of Comparative Example 1.

It was able to confirm from FIGS. 7 and 8 that the load characteristics and lithium ion conductivity of the all-solid-state battery of Example 2 were compared to the all-solid-state battery of Comparative Example 1.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A solid electrolyte comprising:
   Li, Al, P, O, and N,
   wherein the solid electrolyte has a $P_2O_7$ structure, and
   wherein the solid electrolyte is represented by Compositional Formula (1) below:

$$Li_{9+a}Al_{3+b}P_{8-c}O_{29-d}N_e \qquad \text{Compositional Formula (1)}$$

where Compositional Formula (1) satisfies $0 \leq a \leq 5$, $-1 \leq b \leq 1$, $0 \leq c \leq 2$, $0 \leq d \leq 5$, and $0 < e \leq 5$.

2. The solid electrolyte according to claim 1,
   wherein a vibration spectrum originated from the $P_2O_7$ structure is observed at 720 cm$^{-1}$ to 790 cm$^{-1}$ in cm infrared spectroscopy.

3. The solid electrolyte according to claim 1,
   wherein an amount of N is 8 atm % or less.

4. An all-solid-state battery comprising:
   a cathode active material layer;
   an anode active material layer; and
   a solid electrolyte layer disposed between the cathode active material layer and the anode active material layer,
   wherein the solid electrolyte layer is a layer formed of the solid electrolyte according to claim 1.

* * * * *